United States Patent [19]

Ishida et al.

[11] Patent Number: 5,698,751

[45] Date of Patent: Dec. 16, 1997

[54] BRANCHED POLYENE COMPOUNDS AND PRODUCTION THEREOF

[75] Inventors: Tatsuyoshi Ishida; Masaaki Yasuda; Hitoshi Ohnishi; Noriaki Kihara; Toshihiro Sagane; Toshiyuki Tsutsui, all of Kuga-gun, Japan

[73] Assignee: Mitsui Petrochemical Industries, Ltd., Tokyo, Japan

[21] Appl. No.: 498,598

[22] Filed: Jul. 6, 1995

[30] Foreign Application Priority Data

Jul. 6, 1994 [JP] Japan .................................. 6-154952
Mar. 31, 1995 [JP] Japan .................................. 7-075289

[51] Int. Cl.$^6$ .............................. C07C 11/12; C07C 2/02
[52] U.S. Cl. .............................. 585/16; 585/17; 585/18; 585/506; 585/507; 585/509
[58] Field of Search .................. 585/16, 17, 18, 585/506, 507, 509

[56] References Cited

PUBLICATIONS

Barluenga et al., Journal of Organic Chemistry, vol. 46, No. 13, pp. 2721–2726 (1981).

Primary Examiner—Elizabeth D. Wood

[57] ABSTRACT

A branched polyene compound represented by the formula

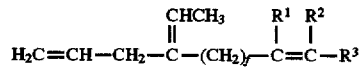

wherein f is an integer of 1–5; $R^1$ and $R^2$ represent hydrogen atoms or alkyl groups of 1–5 carbons; $R^3$ represents a hydrogen atom or an alkyl group of 1–5 carbons or an alkenyl group represented by the formula

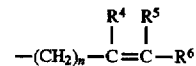

wherein n is an integer of 1–5; $R^4$, $R^5$ and $R^6$ represent hydrogen atoms or alkyl groups of 1–5 carbons; all of $R^1$, $R^2$, $R^3$ are not simultaneously hydrogen atoms; and all of $R^4$, $R^5$ and $R^6$ are not simultaneously hydrogen atoms.

17 Claims, No Drawings

BRANCHED POLYENE COMPOUNDS AND PRODUCTION THEREOF

BACKGROUND OF THE INVENTION

This invention relates to novel branched polyene compounds and production thereof. In general, the polyene compound is a hydrocarbon which has two or more carbon-carbon double bonds in the molecule. A number of such polyene compounds are already known, among which are, for example, 1,3-butadiene, 1,3-pentadiene, 1,4-hexadiene, ethylidene-2-norbornene or dicyclopentadiene.

As one of the important uses, the polyene compound is copolymerized with an α-olefin such as ethylene or propylene to provide an ethylenically unsaturated rubber copolymer which is vulcanizable with, for example, sulfur. Such an ethylenically unsaturated rubber copolymer has excellent resistance to weather, heat and ozone so that it is in wide use as automobile parts, electric insulations, civil and building materials, rubber products such as rubberized fabrics, materials for polymer blending with thermoplastic polymers such as polypropylene or polystyrene.

Among the ethylenically unsaturated rubber copolymers, ethylene/propylene/5-ethylidene-2-norbornene copolymer is particularly in wide use since it has higher vulcanizing rate than the other unsaturated rubber copolymers. However, all the known ethylenically unsaturated rubber copolymers including the above mentioned ethylene/propylene/5-ethylidene-2-norbornene copolymer are slower in vulcanizing rates than usual diene rubbers such as natural rubbers, styrene/butadiene rubbers, isoprene rubbers, butadiene rubers or nitrile rubbers, and hence are of poor covulcanizability with the diene rubbers.

Furthermore, on account of slow vulcanizing rates, it is difficult to carry out vulcanization of the ethylenically unsaturated rubber copolymers within a short period of time or at low temperatures, and consequently the production of vulcanized products of the known unsaturated rubber copolymers is accompanied by low productivity.

SUMMARY OF THE INVENTION

It is an object of the invention to provide novel branched polyene compounds which provide, by copolymerization with α-olefins such as ethylene or propylene, ethylenically unsaturated rubber copolymers which have not only excellent resistance to weather, heat and ozone but also high vulcanizing rates.

It is a further object of the invention to provide a method for the production of such branched polyene compounds.

The invention provides a branched polyene compound represented by the formula

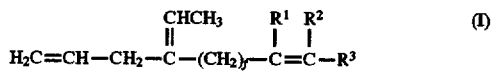

wherein f is an integer of 1–5; $R^1$ and $R^2$ represent 8 hydrogen atoms or alkyl groups of 1–5 carbons; $R^3$ represents a hydrogen atom or an alkyl group of 1–5 carbons or an alkenyl group represented by the formula

wherein n is an integer of 1–5; $R^4$, $R^5$ and $R^6$ represent hydrogen atoms or alkyl groups of 1–5 carbons; all of $R^1$, $R^2$ and $R^3$ are not simultaneously hydrogen atoms; and all of $R^4$, $R^5$ and $R^6$ are not simultaneously hydrogen atoms.

DESCRIPTION OF THE PREFERRED EMBODIMENTS

When $R^1$, $R^2$, $R^3$, $R^4$, $R^5$ or $R^6$ is an alkyl group of 1–5 carbons, the alkyl group may be methyl, ethyl, n-propyl, isopropyl, n-butyl, isobutyl, sec-butyl, t-butyl, n-pentyl or isopentyl. However, the alkyl group has preferably 1–3 carbons, and it is preferred that the alkyl group is methyl or ethyl.

More specifically, the branched polyene compound of a first group of the invention is represented by the formula (I) wherein f is an integer of 1–5; $R^1$, $R^2$ and $R^3$ represent hydrogen atoms or alkyl groups of 1–5 carbons; and all of $R^1$, $R^2$ and $R^3$ are not simultaneously hydrogen atoms.

It is preferred that $R^1$ and $R^2$ are independently hydrogen atoms or alkyl groups of 1–5 carbons; and $R^3$ is an alkyl group of 1–5 carbons. When $R^1$, $R^2$ or $R^3$ is an alkyl group, it is more preferred that the alkyl group has 1–3 carbons and f is an integer of 2–5. It is most preferred that the alkyl group is methyl or ethyl.

The branched polyene compound of the first group of the invention includes the following:

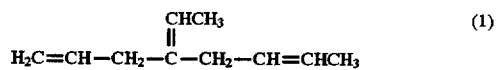 (1)

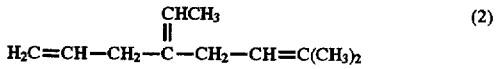 (2)

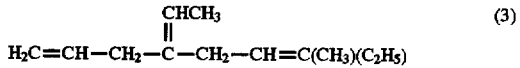 (3)

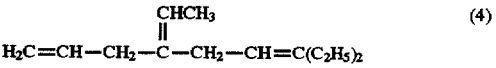 (4)

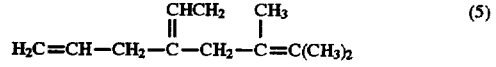 (5)

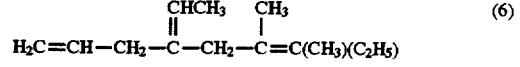 (6)

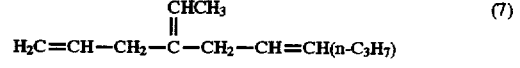 (7)

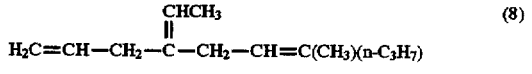 (8)

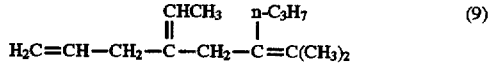 (9)

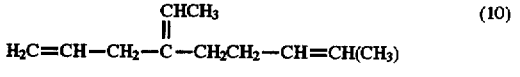 (10)

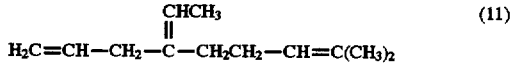 (11)

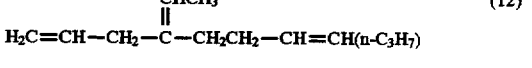 (12)

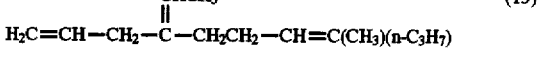 (13)

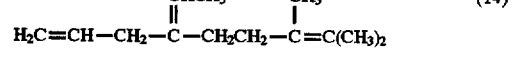 (14)

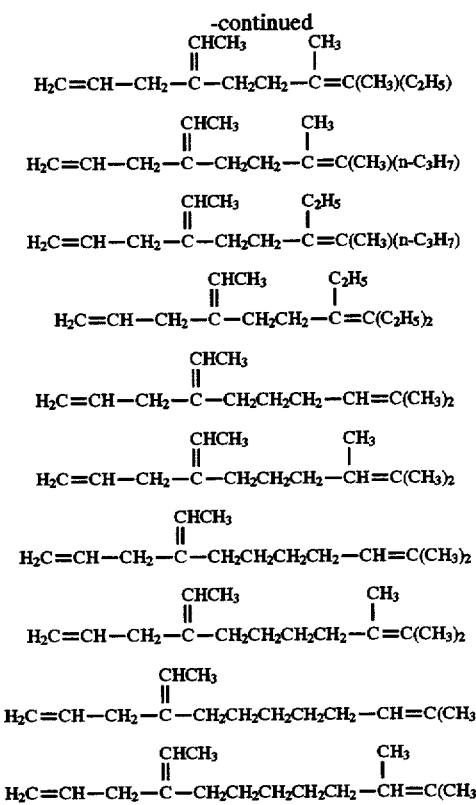

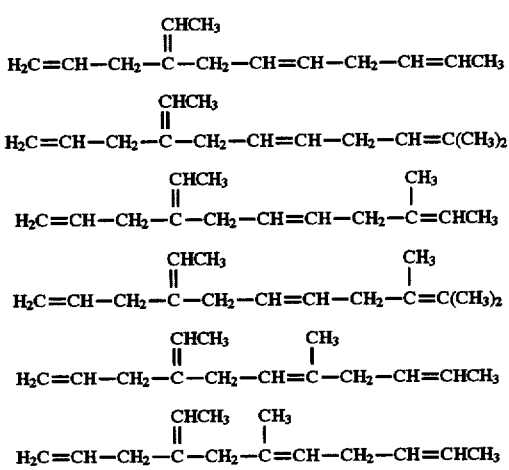

In turn, the branched polyene compound of a second group of the invention is represented by the formula (I′)

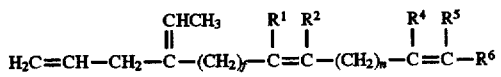

wherein f is an integer of 1–5; n is an integer of 1–5; $R^1$, $R^2$, $R^4$, $R^5$ and $R^6$ represent hydrogen atoms or alkyl groups of 1–5 carbons; and all of $R^4$, $R^5$ and $R^6$ are not simultaneously hydrogen atoms.

When $R^1$, $R^2$, $R^4$, $R^5$ or $R^6$ is an alkyl group, it is preferred that the alkyl group has 1–3 carbons. It is most preferred that the alkyl group is methyl or ethyl, and f is an integer of 1–3, while n is is an integer of 2–4.

The branched polyene compound of the second group of the invention includes the following:

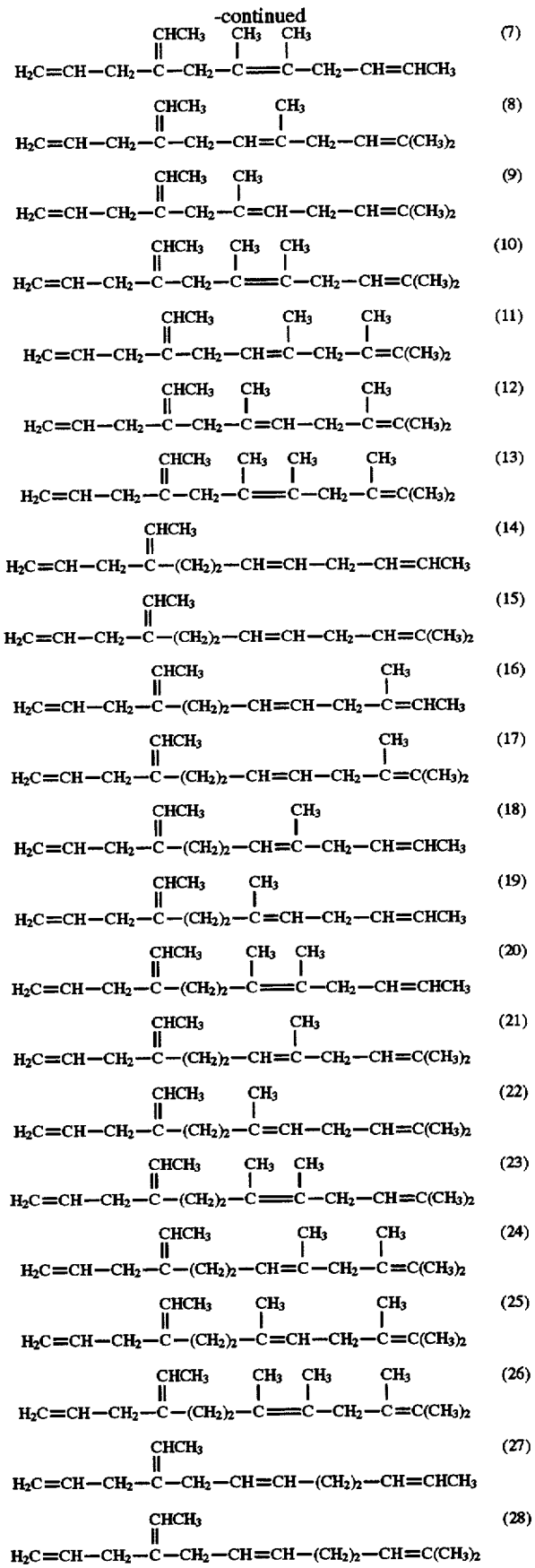

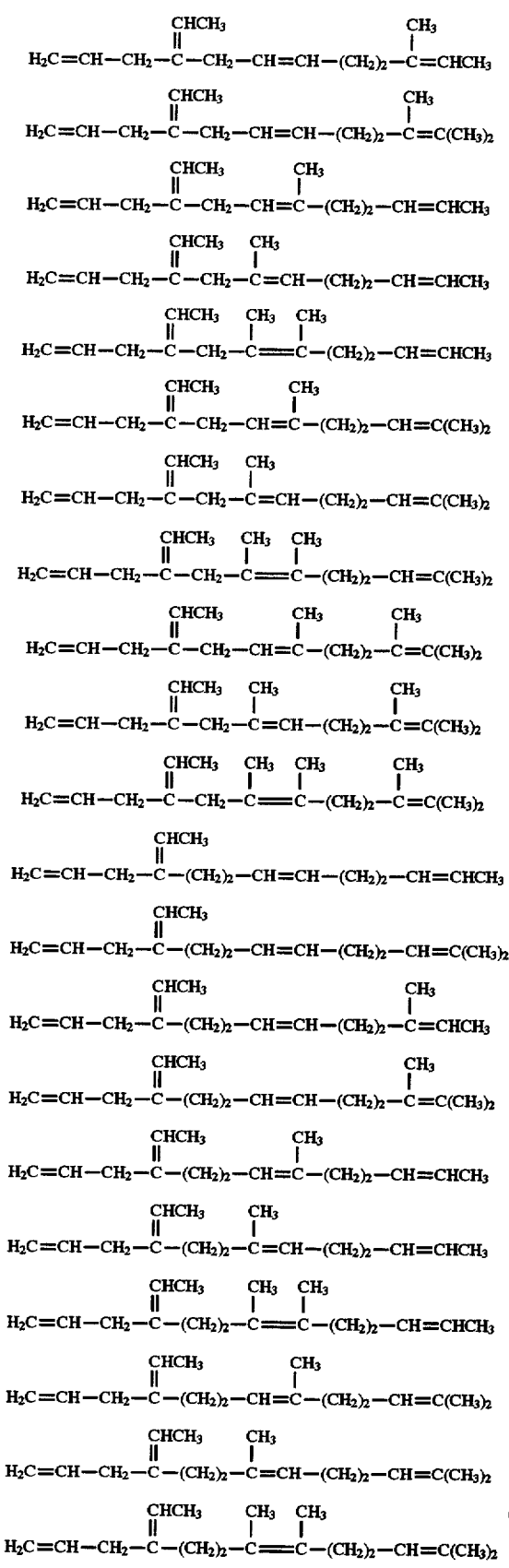
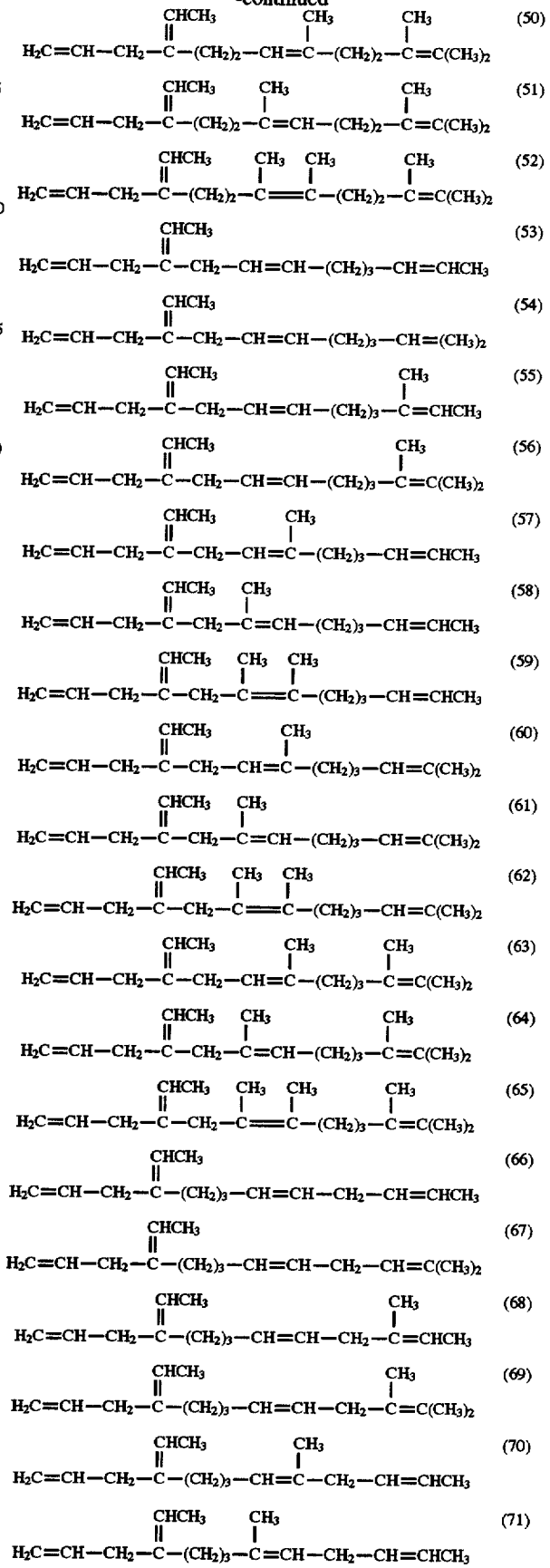

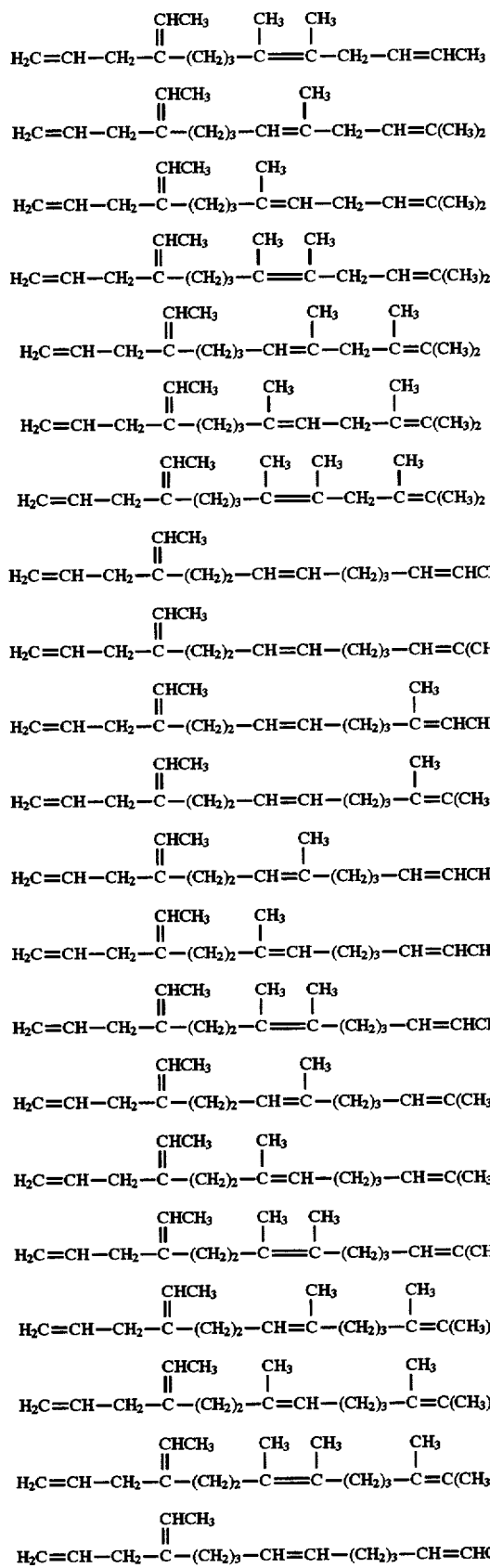
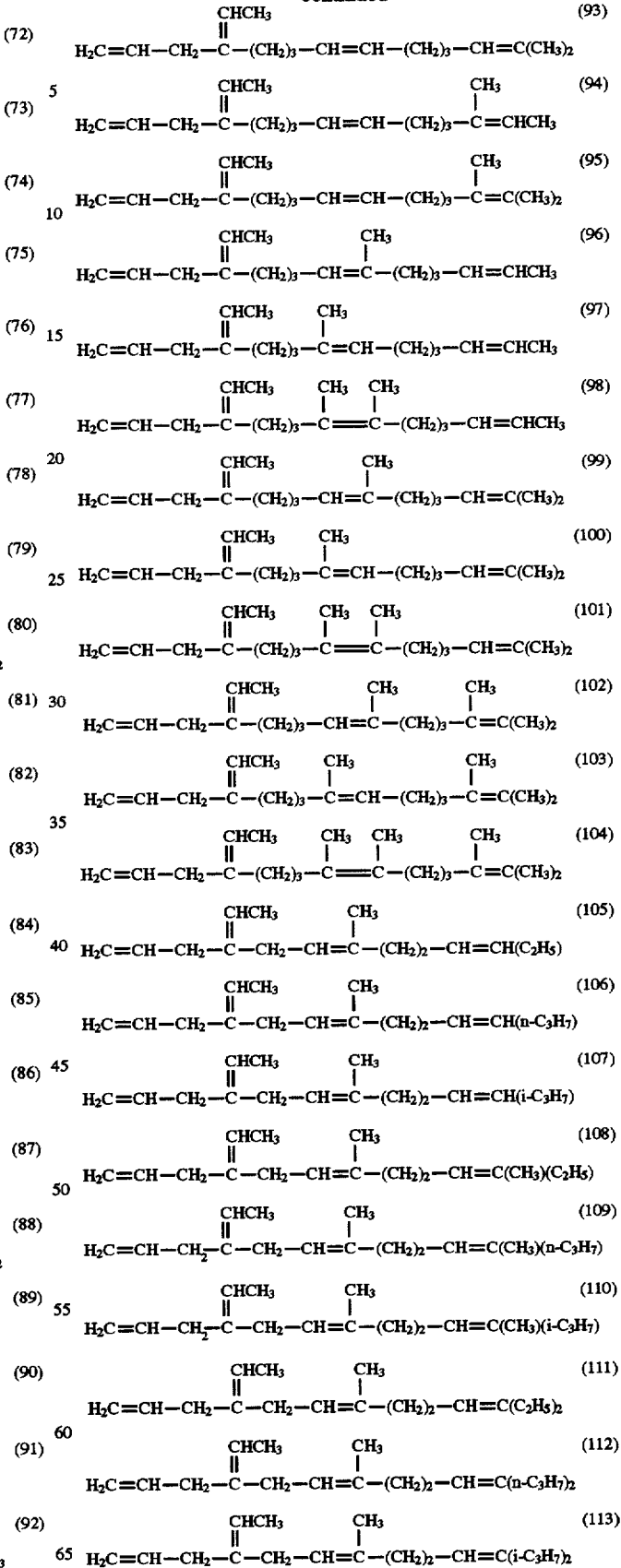

$$H_2C=CH-CH_2-\underset{\underset{CHCH_3}{\|}}{C}-(CH_2)_2-CH=\underset{\underset{CH_3}{|}}{C}-CH_2-CH=CH(C_2H_5) \quad (114)$$

$$H_2C=CH-CH_2-\underset{\underset{CHCH_3}{\|}}{C}-(CH_2)_2-CH=\underset{\underset{CH_3}{|}}{C}-CH_2-CH=CH(n\text{-}C_3H_7) \quad (115)$$

$$H_2C=CH-CH_2-\underset{\underset{CHCH_3}{\|}}{C}-(CH_2)_2-CH=\underset{\underset{CH_3}{|}}{C}-CH_2-CH=CH(i\text{-}C_3H_7) \quad (116)$$

$$H_2C=CH-CH_2-\underset{\underset{CHCH_3}{\|}}{C}-(CH_2)_2-CH=\underset{\underset{CH_3}{|}}{C}-CH_2-CH=C(CH_3)(C_2H_5) \quad (117)$$

$$H_2C=CH-CH_2-\underset{\underset{CHCH_3}{\|}}{C}-(CH_2)_2-CH=\underset{\underset{CH_3}{|}}{C}-CH_2-CH=C(CH_3)(n\text{-}C_3H_7) \quad (118)$$

$$H_2C=CH-CH_2-\underset{\underset{CHCH_3}{\|}}{C}-(CH_2)_2-CH=\underset{\underset{CH_3}{|}}{C}-CH_2-CH=C(CH_3)(i\text{-}C_3H_7) \quad (119)$$

$$H_2C=CH-CH_2-\underset{\underset{CHCH_3}{\|}}{C}-(CH_2)_2-CH=\underset{\underset{CH_3}{|}}{C}-CH_2-CH=C(C_2H_5)_2 \quad (120)$$

$$H_2C=CH-CH_2-\underset{\underset{CHCH_3}{\|}}{C}-(CH_2)_2-CH=\underset{\underset{CH_3}{|}}{C}-CH_2-CH=C(n\text{-}C_3H_7)_2 \quad (121)$$

$$H_2C=CH-CH_2-\underset{\underset{CHCH_3}{\|}}{C}-(CH_2)_2-CH=\underset{\underset{CH_3}{|}}{C}-CH_2-CH=C(i\text{-}C_3H_7)_2 \quad (122)$$

$$H_2C=CH-CH_2-\underset{\underset{CHCH_3}{\|}}{C}-(CH_2)_2-CH=\underset{\underset{CH_3}{|}}{C}-(CH_2)_2-CH=CHC_2H_5 \quad (123)$$

$$H_2C=CH-CH_2-\underset{\underset{CHCH_3}{\|}}{C}-(CH_2)_2-CH=\underset{\underset{CH_3}{|}}{C}-(CH_2)_2-CH=CH(n\text{-}C_3H_7) \quad (124)$$

$$H_2C=CH-CH_2-\underset{\underset{CHCH_3}{\|}}{C}-(CH_2)_2-CH=\underset{\underset{CH_3}{|}}{C}-(CH_2)_2-CH=CH(i\text{-}C_3H_7) \quad (125)$$

$$H_2C=CH-CH_2-\underset{\underset{CHCH_3}{\|}}{C}-(CH_2)_2-CH=\underset{\underset{CH_3}{|}}{C}-(CH_2)_2-CH=\underset{\underset{CH_3}{|}}{C}(C_2H_5) \quad (126)$$

$$H_2C=CH-CH_2-\underset{\underset{CHCH_3}{\|}}{C}-(CH_2)_2-CH=\underset{\underset{CH_3}{|}}{C}-(CH_2)_2-CH=\underset{\underset{CH_3}{|}}{C}(n\text{-}C_3H_7) \quad (127)$$

$$H_2C=CH-CH_2-\underset{\underset{CHCH_3}{\|}}{C}-(CH_2)_2-CH=\underset{\underset{CH_3}{|}}{C}-(CH_2)_2-CH=\underset{\underset{CH_3}{|}}{C}(i\text{-}C_3H_7) \quad (128)$$

$$H_2C=CH-CH_2-\underset{\underset{CHCH_3}{\|}}{C}-(CH_2)_2-CH=\underset{\underset{CH_3}{|}}{C}-(CH_2)_2-CH=C(C_2H_5)_2 \quad (129)$$

$$H_2C=CH-CH_2-\underset{\underset{CHCH_3}{\|}}{C}-(CH_2)_2-CH=\underset{\underset{CH_3}{|}}{C}-(CH_2)_2-CH=C(n\text{-}C_3H_7)_2 \quad (130)$$

$$H_2C=CH-CH_2-\underset{\underset{CHCH_3}{\|}}{C}-(CH_2)_2-CH=\underset{\underset{CH_3}{|}}{C}-(CH_2)_2-CH=C(i\text{-}C_3H_7)_2 \quad (131)$$

$$H_2C=CH-CH_2-\underset{\underset{CHCH_3}{\|}}{C}-CH_2-CH=\underset{\underset{CH_3}{|}}{C}-(CH_2)_3-CH=CH(C_2H_5) \quad (132)$$

$$H_2C=CH-CH_2-\underset{\underset{CHCH_3}{\|}}{C}-CH_2-CH=\underset{\underset{CH_3}{|}}{C}-(CH_2)_3-CH=CH(n\text{-}C_3H_7) \quad (133)$$

$$H_2C=CH-CH_2-\underset{\underset{CHCH_3}{\|}}{C}-CH_2-CH=\underset{\underset{CH_3}{|}}{C}-(CH_2)_3-CH=CH(i\text{-}C_3H_7) \quad (134)$$

$$H_2C=CH-CH_2-\underset{\underset{CHCH_3}{\|}}{C}-CH_2-CH=\underset{\underset{CH_3}{|}}{C}-(CH_2)_3-CH=\underset{\underset{CH_3}{|}}{C}(C_2H_5) \quad (135)$$

$$H_2C=CH-CH_2-\underset{\underset{CHCH_3}{\|}}{C}-CH_2-CH=\underset{\underset{CH_3}{|}}{C}-(CH_2)_3-CH=\underset{\underset{CH_3}{|}}{C}(n\text{-}C_3H_7) \quad (136)$$

$$H_2C=CH-CH_2-\underset{\underset{CHCH_3}{\|}}{C}-CH_2-CH=\underset{\underset{CH_3}{|}}{C}-(CH_2)_3-CH=\underset{\underset{CH_3}{|}}{C}(i\text{-}C_3H_7) \quad (137)$$

$$H_2C=CH-CH_2-\underset{\underset{CHCH_3}{\|}}{C}-CH_2-CH=\underset{\underset{CH_3}{|}}{C}-(CH_2)_3-CH=C(C_2H_5)_2 \quad (138)$$

$$H_2C=CH-CH_2-\underset{\underset{CHCH_3}{\|}}{C}-CH_2-CH=\underset{\underset{CH_3}{|}}{C}-(CH_2)_3-CH=C(n\text{-}C_3H_7)_2 \quad (139)$$

$$H_2C=CH-CH_2-\underset{\underset{CHCH_3}{\|}}{C}-CH_2-CH=\underset{\underset{CH_3}{|}}{C}-(CH_2)_3-CH=C(i\text{-}C_3H_7)_2 \quad (140)$$

$$H_2C=CH-CH_2-\underset{\underset{CHCH_3}{\|}}{C}-(CH_2)_2-\underset{\underset{C_2H_5}{|}}{C}=CH-CH_2-CH=C(CH_3)_2 \quad (141)$$

$$H_2C=CH-CH_2-\underset{\underset{CHCH_3}{\|}}{C}-(CH_2)_2-\underset{\underset{C_2H_5}{|}}{C}=CH-(CH_2)_2-CH=C(CH_3)_2 \quad (142)$$

$$H_2C=CH-CH_2-\underset{\underset{CHCH_3}{\|}}{C}-(CH_2)_2-\underset{\underset{C_2H_5}{|}}{C}=CH-CH_2-CH=C(C_2H_5)_2 \quad (143)$$

$$H_2C=CH-CH_2-\underset{\underset{CHCH_3}{\|}}{C}-(CH_2)_2-CH=\underset{\underset{C_2H_5}{|}}{C}-(CH_2)_2-CH=C(C_2H_5)_2 \quad (144)$$

$$H_2C=CH-CH_2-\underset{\underset{CHCH_3}{\|}}{C}-(CH_2)_2-CH=\underset{\underset{n\text{-}C_3H_7}{|}}{C}-(CH_2)_2-CH=C(CH_3)_2 \quad (145)$$

$$H_2C=CH-CH_2-\underset{\underset{CHCH_3}{\|}}{C}-(CH_2)_2-CH=\underset{\underset{i\text{-}C_3H_7}{|}}{C}-(CH_2)_2-CH=C(CH_3)_2 \quad (146)$$

$$H_2C=CH-CH_2-\underset{\underset{CHCH_3}{\|}}{C}-(CH_2)_2-\underset{\underset{n\text{-}C_3H_7}{|}}{C}=CH-(CH_2)_2-CH=C(CH_3)_2 \quad (147)$$

$$H_2C=CH-CH_2-\underset{\underset{CHCH_3}{\|}}{C}-(CH_2)_2-\underset{\underset{i\text{-}C_3H_7}{|}}{C}=CH-(CH_2)_2-CH=C(CH_3)_2 \quad (148)$$

$$H_2C=CH-CH_2-\underset{\underset{CHCH_3}{\|}}{C}-(CH_2)_2-CH=\underset{\underset{C_2H_5}{|}}{C}-(CH_2)_2-\underset{\underset{CH_3}{|}}{C}=CHCH_3 \quad (149)$$

$$H_2C=CH-CH_2-\underset{\underset{CHCH_3}{\|}}{C}-(CH_2)_2-\underset{\underset{C_2H_5}{|}}{C}=CH-(CH_2)_2-\underset{\underset{CH_3}{|}}{C}=CHCH_3 \quad (150)$$

$$H_2C=CH-CH_2-\underset{\underset{CHCH_3}{\|}}{C}-(CH_2)_2-CH=\underset{\underset{n\text{-}C_3H_7}{|}}{C}-(CH_2)_2-\underset{\underset{CH_3}{|}}{C}=CHCH_3 \quad (151)$$

$$H_2C=CH-CH_2-\underset{\underset{CHCH_3}{\|}}{C}-(CH_2)_2-CH=\underset{\underset{i\text{-}C_3H_7}{|}}{C}-(CH_2)_2-\underset{\underset{CH_3}{|}}{C}=CHCH_3 \quad (152)$$

$$H_2C=CH-CH_2-\underset{\underset{CHCH_3}{\|}}{C}-(CH_2)_2-\underset{\underset{n\text{-}C_3H_7}{|}}{C}=CH-(CH_2)_2-\underset{\underset{CH_3}{|}}{C}=CHCH_3 \quad (153)$$

$$H_2C=CH-CH_2-\underset{\underset{CHCH_3}{\|}}{C}-(CH_2)_2-\underset{\underset{i\text{-}C_3H_7}{|}}{C}=CH-(CH_2)_2-\underset{\underset{CH_3}{|}}{C}=CHCH_3 \quad (154)$$

The chemical structure of these branched polyene compounds of the invention of either groups can be determined by mass spectrometry, infrared spectrophotometry, proton nuclear magnetic resonance spectrometry or any other suitable means.

The branched polyene compounds of the invention usually has stereoisomers, i.e., the trans- and the cis-isomers. Any mixture of such isomers may be used for the production of ethylenically unsaturated rubber copolymers, however, a single isomer may be used if necessary.

The branched polyene compounds of the invention is produced according to the invention by reacting ethylene with a conjugated diene compound represented by the formula

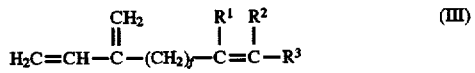  (III)

wherein f is an integer of 1–5; $R^1$ and $R^2$ represent hydrogen atoms or alkyl groups of 1–5 carbons; $R^3$ represent a hydrogen atom or an alkyl group of 1–5 carbons or an alkenyl group represented by the formula

  (II)

wherein n is an integer of 1–5; $R^4$, $R^5$ and $R^6$ represent hydrogen atoms or alkyl groups of 1–5 carbons; all of $R^1$, $R^2$ and $R^3$ are not simultaneously hydrogen atoms; and all of $R^4$, $R^5$ and $R^6$ are not simultaneously hydrogen atoms.

According to a preferred embodiment, the branched polyene compounds of the first group of the invention is produced by reacting ethylene with a conjugated diene compound represented by the formula (III) wherein f is an integer of 1–5; $R^1$, $R^2$ and $R^3$ are independently hydrogen atoms or alkyl groups of 1–5 carbons; however, all of $R^1$, $R^2$ and $R^3$ are not hydrogen atoms at the same time.

The conjugated diene compound as mentioned above includes, for example, the following compounds.

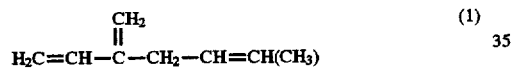  (1)

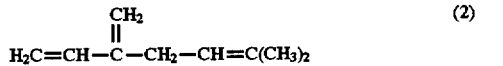  (2)

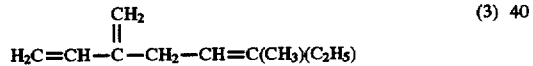  (3)

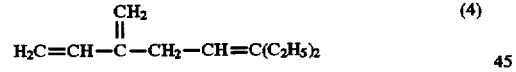  (4)

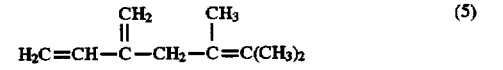  (5)

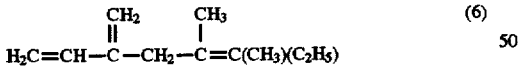  (6)

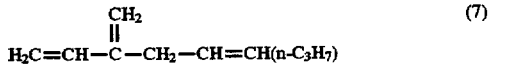  (7)

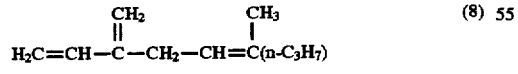  (8)

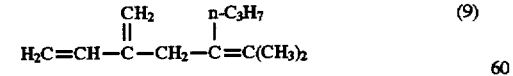  (9)

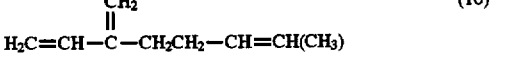  (10)

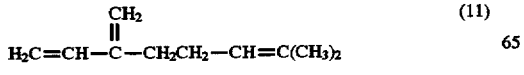  (11)

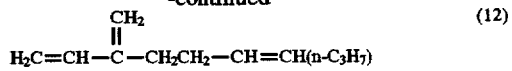  (12)

  (13)

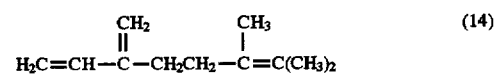  (14)

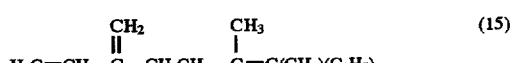  (15)

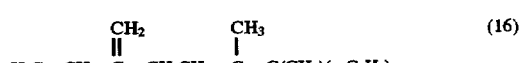  (16)

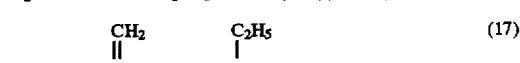  (17)

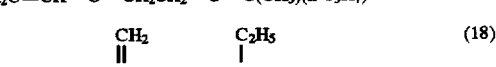  (18)

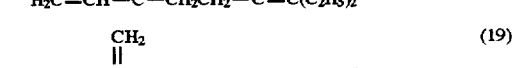  (19)

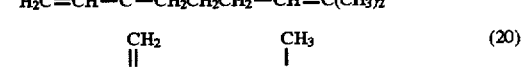  (20)

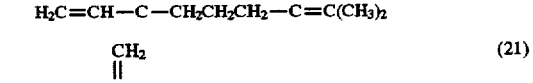  (21)

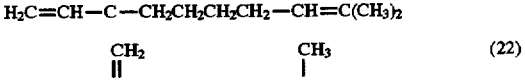  (22)

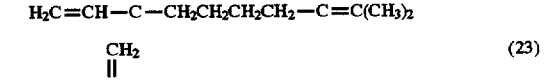  (23)

  (24)

According to a further preferred embodiment, the branched polyene compounds of the second group of the invention is produced by reacting ethylene with a conjugated diene compound represented by the formula (IV)

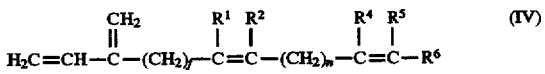  (IV)

wherein f is an integer of 1–5; $R^1$, $R^2$, $R^4$, $R^5$ and $R^6$ represent hydrogen atoms or alkyl groups of 1–5 carbons; and all of $R^4$, $R^5$ and $R^6$ are not hydrogen atoms at the same time.

The conjugated diene compound as mentioned above includes, for example, the following compounds.

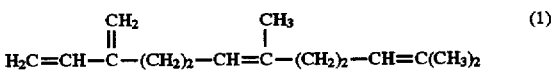  (1)

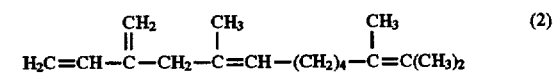  (2)

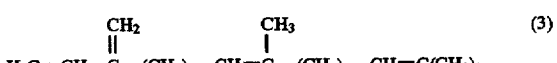  (3)

There is usually produced a mixture of trans- and cis-isomers of the branched polyene compounds by the above mentioned reaction. The trans- and cis-isomers may be separated from each other by distillation, for example, if necessary. As the case may be, only one of the trans- and cis-isomers may be obtained.

Furthermore, the production of the branched polyene compound of the first group may be accompanied by production of a by-product represented by the formula

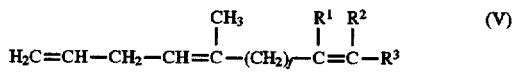

wherein f is an integer of 1–5; $R^1$, $R^2$ and $R^3$ represent hydrogen atoms or alkyl groups of 1–5 carbons; and all of $R^1$, $R^2$ and $R^3$ are not hydrogen atoms at the sametime.

In turn, the production of the branched polyene compound of the second group may be accompanied by production of a by-product represented by the formula

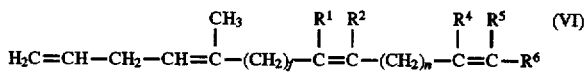

wherein f is an integer of 1–5; n is an integer of 1–5; $R^1$, $R^2$, $R^4$, $R^5$ and $R^6$ represent hydrogen atoms or alkyl groups of 1–5 carbons; and all of $R^4$, $R^5$ and $R^6$ are not hydrogen atoms at the same time.

These by-products may be removed from the target polyene compounds, if necessary, by means of distillation or any other suitable means. However, a mixture of the branched polyene compound and the by-products may be used with no problem for the production of ethylenically unsaturated rubber copolymers.

The reaction for the production of the branched polyene compounds of the invention is carried out by placing a conjugated diene compound in a closed vessel, adding ethylene into the vessel, and then heating the mixture at a temperature usually of 50°–200° C., preferably of 70°–150° C., over a period of 0.5–30 hours, under stirring, preferably under an atmosphere of an inert gas such as nitrogen or argon. The reaction is carried out at an ethylene pressure of 0.5–100 kg/cm², preferably of 1–50 kg/cm². Ethylene may be added into the reaction vessel intermittently or continuously.

A reaction solvent may or may not be used. If used, preferred solvent may be a hydrocarbon solvent such as hexane, heptane, octane, nonane, decane, undecane, dodecane, toluene or xylene. These solvents are merely illustrative.

It is preferred that the reaction of ethylene with a conjugated diene compound is carried out in the presence of a catalyst which is prepared by the reaction of a transition metal compound with an organoaluminum compound. The transition metal compound usable includes, for example, chlorides, bromides, acetylacetonates, 1,1,1,5,5,5-hexafluoroacetylacetonates or dipivaloylmethanes of metals of the iron group such as iron or ruthenium, metals of the cobalt group such as cobalt, rhodium or iridium, or metals of the nickel group such as nickel or palladium. Among these compounds, those of iron, cobalt, nickel, rhodium or palladium are preferred, with those of cobalt being most preferred, in particular, cobalt chloride.

The transition metal compound as above mentioned may be used as it is for the preparation of the catalyst, but it is preferred that the transition metal compound is used as a transition metal complex or a coordination compound which has organic ligands coordinated to the metal. Namely, a transition metal compound is used together with an organic compound which acts as ligands, i.e., an organic ligand, for the transition metal when the catalyst is prepared. Alternatively, a transition metal compound is separatedly reacted with an organic ligand to prepare a transition metal complex and the complex is then reacted with an organoaluminum compound to prepare a catalyst.

The organic ligand for the transition metal includes, for example:
bis(diphenylphosphino)methane,
1,2-bis(diphenylphosphino)ethane,
1,3-bis(diphenylphosphino)propane,
1,4-bis(diphenylphosphino)butane,
triethylphosphine, tributylphosphine, triphenylphosphine, cyclooctadiene or cyclooctatetraene.

The transition metal complex which has ligands bonded to the metal by coordination bond includes, for example:
[1,2-bis(diphenylphosphino)ethane]cobalt (II) chloride,
[1,2-bis(diphenylphosphino)ethane]nickel (II) chloride or
bis(triphenylphosphine)nickel (II) chloride.

The organoaluminun compound includes, for example, trimethylaluminum, dimethylaluminum chloride, triethylaluninum, diethylaluminum chloride, diethylaluminum ethoxide, ethylaluminum dichloride or triisobutylaluminum, among which triethylaluminum is particularly preferred. The organoaluminum compound may be used as it is or as a solution in a hydrocarbon solvent such as toluene or hexane.

For the preparation of catalyst, a transition metal compound is used in an amount of 0.001–10 mols, preferably 0.01–1 mols per 100 mols of conjugated diene compound, whereas an organic ligand is used in an amount of less than 20 mols, preferably 0.1–5 mols, per mol of the transition metal compound. The organoaluninun compound is used in an amount of 1–200 mols, preferably 3–100 mols per mole of the transition metal compound. When a transition metal complex is used, it is used in an amount of 0.001–10 mols, preferably 0.01–1 mols per 100 mols of conjugated diene compound.

The catalyst may be prepared in situ in the reaction system where ethylene and the conjugated diene compound are present by reacting the transition metal compound or complex with the organoaluminum compound. Alternatively, the catalyst may be prepared in advance by reacting the transition metal compound or complex with the organoaluminum compound, and is then used in the reaction.

By way of example, the catalyst is prepared by admixing a transition metal compound with an organic ligand at room temperatures in a reaction solvent such as decane under an inert gas atmosphere, and an organoaluminum compound is then added to the reaction mixture, followed by stirring the resultant mixture at room temperatures. More simply, the catalyst is prepared by reacting a transition metal complex with an organoaluminum compound in a reaction solvent at room temperature under an inert gas atmosphere.

The invention will be set forth in more detail with reference to examples which are however illstrative only, and the invention is not limited thereto.

A. Production of Branched Polyene Compounds of the First Group

EXAMPLE 1

(Preparation of Catalyst)

An amount of 43 mg (0.33 mmol) of anhydrous cobalt (II) chloride, 263 mg (0.66 mmol) of 1,2-bis (diphenylphosphino)ethane and 23 ml of anhydrous decane were placed in a 50 ml capacity flask containing a magnetic stirrer under an argon atmosphere, and the mixture was stirred at 25° C. for two hours. An amount of 17 ml of 1 mol/l touene solution of triethylaluminum (17 mmol of triethylaluminum) was then added to the mixture at the same temperature and the resultant mixture was stirred for two hours, thereby to prepare a catalyst.

(Synthesis of 4-ethylidene-8-methyl-1,7-nonadiene)

An amount of 100 g (734 mmol) of 7-methyl-3-methylene-1,6-octadiene (β-myrcene) and all the amount of the above-prepared catalyst were placed in a 300 ml capacity stainless steel (SUS 316) autoclave under an argon atmosphere, and the autoclave was closed. Ethylene was then added into the autoclave until it had a pressure of 35 kg/cm$^2$, and the inside the autoclave was gradually heated to 95° C., thereby effecting the reaction over a period of 15 hours. During the reaction ethylene was added into the autoclave five times to compensate the amount of ethylene consumed.

After completion of the reaction, the autoclave was cooled and opened, and the resultant reaction mixture was poured into 100 ml of water, so that an organic layer was separated from an aqueous layer. The organic layer was concentrated with an evaporator by removing low boiling temperature components therefrom, and then distilled with a precise fractionation tower having 20 plates under reduced pressures, to provide 83 g of 4-ethylidene-8-methyl-1,7-nonadiene in a yield of 69% and a conversion rate of β-myrcene of 90%, together with 16 g of 5,9-dimethyl-1,4,8-decatriene, an isomer of the target compound, in a yield of 13%.

4-Ethylidene-8-methyl-1,7-nonadiene:
Boiling Point: 103°–105° C./30 mmHg
GC-MS (Gas Chromatography Mass Spectrometry): 164 (M$^+$), 149, 123, 95, 69, 41, 27
(Gas chromatographic measuring conditions:

Column: J & W Scientific, Capillary Column DB-1701, 0.25 mm×30 m

Vaporizing temperature: 250° C.

Column temperature: Maintained at 60° C. for 5 minutes, and then raised to 200° C. at a rate of 10° C. per minute
Infrared Spectrophotometry (neat, cm$^{-1}$): 3080, 2975, 2925, 2850, 1670, 1640, 1440, 1380, 1235, 1110, 995, 910, 830

Proton Nuclear Magnetic Resonance Spectrometry (solvent: CDCl$_3$, ppm):
1.59 (3H, doublet, J=7 Hz) 1.60 (3H, singlet) 1.68 (3H, singlet) 2.00 (2H, multipet) 2.06 (2H, multipet) 2.80 (2H, doublet, J=7 Hz) 4.9–5.2 (3H, multipet) 5.30 (1H, quartet, J=7 Hz) 5.75 (1H, multipet)

EXAMPLE 2

An amount of 174 mg (0.33 mmol) of [1,2-bis(diphenylphosphino)ethane]cobalt (II) chloride and 23 ml of anhydrous decane were placed in the same flask as used in Example 1 under an argon atmosphere, and the mixture was stirred at 25° C. for two hours. An amount of 17 ml of 1 mol/l touene solution of triethylaluminum (17 mmol of triethylaluninum) was then added to the mixture at the same temperature and the resultant mixture was stirred for two hours, thereby to prepare a catalyst.

The above catalyst was used and the otherwise in the same manner as in Example 1, the reaction was carried out, to provide 4-ethylidene-8-methyl-1,7-nonadiene in a yield of 65% and a conversion rate of β-myrcene of 88%, together with 5,9-dimethyl-1,4,8-decatriene, an isomer of the target compound, in a yield of 12%.

EXAMPLE 3

An amount of 174 mg (0.33 mmol) of [1,2-bis(diphenylphosphino)ethane]nickel (II) chloride and 23 ml of anhydrous decane were placed in the same flask as used in Example 1 under an argon atmosphere, and the mixture was stirred at 25° C. for two hours. An amount of 17 ml of 1 mol/l touene solution of triethylaluminum (17 mmol of triethylaluminum) was then added to the mixture at the same temperature and the resultant mixture was stirred for two hours, thereby to prepare a catalyst.

The above catalyst was used and the otherwise in the same manner as in Example 1, the reaction was carried out, to provide 4-ethylidene-8-methyl-1,7-nonadiene in a yield of 41% and a conversion rate of β-myrcene of 57%, together with 5,9-dimethyl-1,4,8-decatriene, an isomer of the target compound, in a yield of 10%.

EXAMPLE 4

An amount of 117 mg (0.33 mmol) of iron (III) acetylacetonate and 23 ml of anhydrous decane were placed in the same flask as used in Example 1 under an argon atmosphere, and the mixture was stirred at 25° C. for two hours. An amount of 17 ml of 1 mol/l touche solution of triethylaluminum (17 mmol of triethylaluminum) was then added to the mixture at the same temperature and the resultant mixture was stirred for two hours, thereby to prepare a catalyst.

The reaction was carried out by use of the above catalyst and the otherwise in the same manner as in Example 1, to provide 4-ethylidene-8-methyl-1,7-nonadiene in a yield of 17% and a conversion rate of β-myrcene of 35%, together with 5,9-dimethyl-1,4,8-decatriene, an isomer of the target compound, in a yield of 8%.

EXAMPLE 5

(Synthesis of 4-ethylidene-10,11-dimethyl-1,10-tridecadiene)

An amount of 103 g (500 mmol) of 9,10-dimethyl-3methylene-1,9-dodecadiene, 174 mg (0.33 mmol) of [1,2-bis(diphenylphosphino)ethane]cobalt (II) chloride and 15 ml of 1 mol/l hexane solution of triethylaluminum (15 mmol of triethylaluminum) were placed in a 300 ml capacity stainless steel (SUS 316) autoclave under a nitrogen atmosphere, and the mixture was stirred at room temperatures for 30 minutes to prepare a catalyst.

Ethylene was then added into the autoclave until it had a pressure of 10 kg/cm$^2$, and the inside the autoclave was gradually heated to 80° C., thereby to effect the reaction for two hours. During the reaction ethylene was added into the autoclave twice to compensate the amount of ethylene consumed.

After completion of the reaction, the autoclave was cooled and opened, and the resultant reaction mixture was poured into 100 ml of water, so that an organic layer was separated from an aqueous layer. The organic layer was concentrated with an evaporator by removing low boiling temperature components therefrom, and then distilled with a precise fractionation tower having 20 plates under reduced pressures, to provide 84 g of 4-ethylidene-10,11-dimethyl-1,10-tridecadiene in a yield of 72% and a conversion rate of the starting maerial (9,10-dimethyl-3-methylene-1,9-dodecadiene) of 95%, together with 18 g of 5,11,12-trimethyl-1,4,11-tatradecatriene, an isomer of the target compound, in a yield of 15%.

4-Ethylidene-10,11-dimethyl-1,10-tridecadiene:
Boiling Point: 123°–125° C./2 mmHg
FD-MS (Field Desorption Mass Spectrometry): 234 (M$^+$)
Proton Nuclear Magnetic Resonance Spectrometry (solvent: CDCl$_3$, ppm):
1.00 (3H, triplet, J=7 Hz)

1.3–1.5 (6H, multipet)
1.58 (3H, doublet, J=7 Hz)
1.60 (3H, singlet)
1.63 (3H, singlet)
1.9–2.1 (6H, multipet)
2.30 (2H, doublet, J=7 Hz)
4.9–5.1 (2H, multipet)
5.30 (1H, quartet, J=7 Hz)
5.75 (1H, multipet)

B. Production of Branched Polyene Compounds of the Second Group

EXAMPLE 1

(Preparation of Catalyst)

An amount of 1.05 g (2.00 mmol) of [1,2-bis(diphenylphosphino)ethane]cobalt (II) chloride and 100 ml of anhydrous decane were placed in a 300 ml capacity flask containing a magnetic stirrer under an argon atmosphere, and the mixture was stirred at 25° C. for 30 minutes. An amount of 100 ml of 1 mol/l hexane solution of triethylaluminum (100 mmol of triethylaluminum) was then added to the mixture at the same temperature and the resultant mixture was stirred for two hours to prepare a catalyst.
(Synthesis of 4-ethylidene-8,12-dimethyl-1,7,11-tridecatriene)

An amount of 204.3 g (1.00 mol) of 7,11-dimethyl-3-methylene-1,6,10-dodecatriene (β-farnesene) and all the amount of the above-prepared catalyst were placed in a one liter capacity stainless steel (SUS 316) autoclave under an argon atmosphere, and the autoclave was closed. Ethylene was then added into the autoclave until it had a pressure of 10 kg/cm$^2$, and the inside the autoclave was gradually heated to 95° C., thereby to effect the reaction over a period of 15 hours. During the reaction ethylene was added into the autoclave five times to compensate the amount of ethylene consumed.

After completion of the reaction, the autoclave was cooled and opened, and the resultant reaction mixture was poured into 300 ml of water, so that an organic layer was separated from an aqueous layer. The organic layer was concentrated with an evaporator by removing low boiling temperature components therefrom, and then distilled with a precise fractionation tower having 20 plates under reduced pressures, to provide 153 g of 4-ethylidene-8,12-dimethyl-1,7,11-tridecatriene as a colorless liquid in a yield of 66% and a conversion rate of β-farnesene of 90%, together with 26 g of 5,9,13-trimethyl-1,4,8,12-tetradecatriene in a yield of 11%.

4-Ethylidene-8,12-dimethyl-1,7,11- tridecatriene:

Boiling Point: 116°–125° C./2 mmHg (as a mixture of 4-ethylidene-8,12-dimethyl-1,7,11-tridecatriene and 5,9,13-trimethyl-1,4,8,12-tetradecatraene)
GC-MS (Gas Chromatography Mass Spectrometry): 232 (M$^+$), 217, 189, 163, 148, 121,107, 95, 81, 69
(Gas chromatographic measuring conditions:
Column: J & W Scientific, Capillary Column DB-1701, 0.25 mm×30 m
Column temperature: Maintained at 40° C. for 5 minutes, and then raised to 200° C. at a rate of 5° C. per minute
Injection temperature: 250° C.
Detecting temperature: 300° C. (FID Detector)
Infrared Spectrophotometry (neat, cm$^{-1}$): 3070, 2960, 2920, 2850, 1670, 1640, 1440, 1380, 1235, 1150, 1105, 995, 960, 910, 830

Proton Nuclear Magnetic Resonance Spectrometry (solvent: CDCl$_3$, ppm):
1.58 (3H, doublet, J=7 Hz)
1.60 (6H, singlet)
1.69 (3H, singlet)
2.01 (8H, multipet)
2.78 (2H, doublet, J=7 Hz)
4.9–6.0 (6H, multipet)

EXAMPLE 2

An amount of 0.26 g (2.00 mmol) of anhydrous cobalt (II) chloride was dispersed in 100 ml of anhydrous decane in the same flask as used in Example 1 under an argon atmosphere, and then 1.59 g (4.00 mmol) of 1,2-bis(diphenylphosphino)ethane was added to the dispersion. The mixture was stirred at 25° C. for two hours. An amount of 100 ml of 1 mol/l hexane solution of triethylaluminum (100 mmol of triethylaluminum) was then added to the mixture at the same temperature and the resultant mixture was stirred for two hours, thereby to prepare a catalyst.

The above catalyst was used and the otherwise in the same manner as in Example 1, the reaction was carried out, to provide 4-ethylidene-8,12-dimethyl-1,7,11-tridecatriene in a yield of 60% and a conversion rate of β-farnesene of 87%, together with 5,9,13-trimethyl-1,4,8,12-tetradecatetraene, an isomer of the target compound, in a yield of 8%.

EXAMPLE 3

An amount of 1.05 g (2.00 mmol) of [1,2-bis(diphenylphosphino)ethane]nickel (II) chloride was used in place of the cobalt complex, and the otherwise in the same manner as in Example 1, the reaction was carried out, to provide 4-ethylidene-8,12-dimethyl-1,7,11-tridecatrienein a yield of 43% and a conversion rate of β-farnesene of 61%, together with 5,9,13-trimethyl-1,4,8,12-tetradecatriene, an isomer of the target compound, in a yield of 7%.

EXAMPLE 4

(Synthesis of 4-ethylidene-6,12-dimethyl-1,6,12-tetradecatriene)

An amount of 44 g (200 mmol) of anhydrous 5,11-dimethyl-3-methylene-1,5,11-tridecatriene, 53 mg (0.10 mmol) of [1,2-bis(diphenylphosphino)ethane]cobalt (II) chloride and 5 ml of 1 mol/l toluene solution of triethylaluminum (5 mmol of triethylaluminum) were placed in a 300 ml capacity stainless steel (SUS 316) autoclave under a nitrogen atmosphere, and the mixture was stirred at room temperature for 30 minutes to prepare a catalyst.

Ethylene was then added into the autoclave until it had a pressure of 10 kg/cm$^2$, and the inside the autoclave was gradually heated to 70° C., thereby to effect the reaction over a period of six hours. During the reaction ethylene was added into the autoclave three times to compensate the amount of ethylene consumed.

After completion of the reaction, the autoclave was cooled and opened, and the resultant reaction mixture was poured into 100 ml of water, so that an organic layer was separated from an aqueous layer. The organic layer was concentrated with an evaporator by removing low boiling temperature components therefrom, and then distilled with a precise fractionation tower having 20 plates under reduced pressures, to provide 37 g of 4-ethylidene-6,12-dimethyl-1,6,12-tetradecatriene in a yield of 75% and a conversion rate of the starting material (5,11-dimethyl-3-methylene-1,5,11- tridecatriene) of 95%, together with 6 g of 5,7,13-trimethyl-1,4,7,13-pentadecatetraene, an isomer of the target compound, in a yield of 12%.

4-Ethylidene-6,12-dimethyl-1,6,12-tetradecatriene:
Boiling Point: 125°–127° C./1 mm Hg
FD-MS (Field Desorption Mass Spectrometry): 246 (M$^+$)
Proton Nuclear Magnetic Resonance Spectrometry (solvent: CDCl$_3$, ppm):

1.3–1.4 (4H, multipet)
1.58 (6H, doublet, J=7 Hz)
1.60 (3H, singlet)
1.65 (3H, singlet)
1.9–2.1 (4H, multipet)
2.7–2.8 (4H, multipet)
4.9–5.2 (4H, multipet)
5.32 (1H, quartet, J=7 Hz)
5.77 (1H, multipet)

EXAMPLE 5

(Synthesis of 4-ethylidene-9,14-dimethyl-1,8,13-pentadecatriene)

An amount of 46 g (200 mmol) of anhydrous 8,13-dimethyl-3-methylene-1,7,12-tetradecatriene, 106 mg (0.20 mmol) of [1,2-bis(diphenylphosphino)ethane]cobalt (II) chloride and 5 ml of 1 mol/l toluene solution of triethylaluminum (5 mmol of triethylaluminum) were placed in a 300 ml capacity stainless steel (SUS 316) autoclave under a nitrogen atmosphere, and the mixture was stirred at room temperature for 30 minutes to prepare a catalyst.

Ethylene was then added into the autoclave until it had a pressure of 10 kg/cm$^2$, and the inside the autoclave was gradually heated to 80° C., thereby to effect the reaction over a period of six hours. During the reaction ethylene was added into the autoclave three times to compensate the amount of ethylene consumed.

After completion of the reaction, the autoclave was cooled and opened, and the resultant reaction mixture was poured into 100 ml of water, so that an organic layer was separated from an aqueous layer. The organic layer was concentrated with an evaporator by removing low boiling temperature components therefrom, and then distilled with a precise fractionation tower having 20 plates under reduced pressures, to provide 40 g of 4-ethylidene-9,14-dimethyl-1,8,13-pentadecatriene in a yield of 77% and a conversion rate of the starting material (8,13-dimethyl-3-methylene-1,7,12-tetradecatriene) of 100%, together with 6.8 g of 5,10,15-trimethyl-1,4,9,14-hexadecatetraene, an isomer of the target compound, in a yield of 13%.

4-Ethylidene-9, 14-dimethyl- 1,8,13-pentadecatriene:
Boiling Point: 133°–136° C./1 mmHg
FD-MS (Field Desorption Mass Spectrometry): 260 (M$^{30}$)
Proton Nuclear Magnetic Resonance Spectrometry (solvent: CDCl$_3$, ppm):

1.3–1.4 (4H, multipet)
1.58 (3H, doublet, J=7 Hz)
1.60 (6H, singlet)
1.68 (3H, singlet)
1.9–2.2 (8H, multipet)
2.77 (2H, doublet, J=7 Hz)
4.9–5.2 (411, multipet)
5.30 (1H, quartet, J=7 Hz)
5.74 (1H, multipet)

What is claimed is:

1. A branched polyene compound represented by the formula

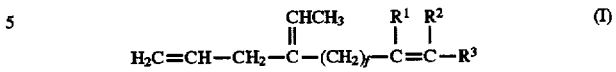

wherein f is an integer of 1–5; R$^1$ and R$^2$ represent hydrogen atoms or alkyl groups of 1–5 carbons; R$^3$ represents a hydrogen atom or an alkyl group of 1–5 carbons or an alkenyl group represented by the formula

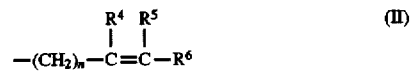

wherein n is an integer 1–5; R$^4$, R$^5$ and R$^6$ represent hydrogen atoms or alkyl groups of 1–5 carbons; all of R$^1$, R$^2$ and R$^3$ are not simultaneously hydrogen atoms; and all of R$^4$, R$^5$ and R$^6$ are not simultaneously hydrogen atoms.

2. A branched polyene compound as claimed in claim 1 which is represented by the formula (I) wherein R$^1$, R$_2$ and R$^3$ represent hydrogen atoms or alkyl groups of 1–5 carbons; and all of R$^1$, R$^2$ and R$^3$ are not simultaneously hydrogen atoms.

3. A branched polyene compound as claimed in claim 1 which is represented by the formula (I) wherein R$^1$, R$^2$ and R$^3$ represent hydrogen atoms or methyl groups or ethyl groups; and all of R$^1$, R$^2$ and R$^3$ are not simultaneously hydrogen atoms.

4. A branched polyene compound as claimed in claim 1 which is represented by the formula (I')

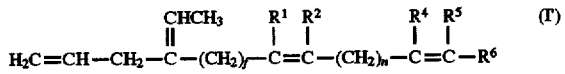

wherein f is an integer of 1–5; n is an integer of 1–5; R$^1$, R$^2$, R$^4$, R$^5$ and R$^6$ represent hydrogen atoms or alkyl groups of 1–5 carbons; and all of R$^4$, R$^5$ and R$^6$ are not simultaneously hydrogen atoms.

5. A branched polyene compound as claimed in claim 4 which is represented by the formula (I') wherein R$^1$, R$^2$, R$^4$, R$^5$ and R$^6$ represent hydrogen atoms or alkyl groups of 1–3 carbons; and all of R$^4$, R$^5$ and R$^6$ are not simultaneously hydrogen atoms.

6. A branched polyene compound as claimed in claim 4 which is represented by the formula (I') wherein R$^1$, R$^2$, R$^4$, R$^5$ and R$^6$ represent hydrogen atoms or methyl groups or ethyl groups; and all of R$^4$, R$^5$ and R$^6$ are not simultaneouly hydrogen atoms.

7. 4-Ethylidene-8-methyl-1,7-nonadiene according to claim 1.

8. 4-Ethylidene-10,11-dimethyl-1,10-tridecadiene according to claim 1.

9. 4-Ethylidene-8,12-dimethyl-1,7,11-tridecatriene according to claim 1.

10. 4-Ethylidene-6,12-dimethyl-1,6,12-tetradecatriene according to claim 1.

11. 4-Ethylidene-9,14-dimethyl-1,8,13-pentadecatriene according to claim 1.

12. A method for producing a branched polyene compound represented by the formula

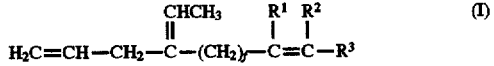

wherein f is an integer of 1–5; R$^1$ and R$^2$ represent hydrogen atoms or alkyl groups of 1–5 carbons; R$^3$ represents a hydrogen atom or an alkyl group of 1–5 carbons or an alkenyl group represented by the formula $$-(CH_2)_n-\underset{R^4}{\underset{|}{C}}=\underset{R^5}{\underset{|}{C}}-R^6 \quad (II)$$

wherein n is an integer of 1–5; $R^4$, $R^5$ and $R^6$ represent hydrogen atoms or alkyl groups of 1–5 carbons; all of $R^1$, $R^2$ and $R^3$ are not simultaneously hydrogen atoms; and all of $R^4$, $R^5$ and $R^6$ are not simultaneously hydrogen atoms, which comprises reacting ethylene with a conjugated diene compound represented by the formula $$H_2C=CH-\underset{\underset{CH_2}{\|}}{C}-(CH_2)_f-\underset{R^1}{\underset{|}{C}}=\underset{R^2}{\underset{|}{C}}-R^3 \quad (III)$$

wherein f, $R^1$, $R^2$ and $R^3$ are the same as above in a reaction vessel at a temperature of 50°–200° C. under an atmosphere of an inert gas and under an ethylene pressure of 0.5–100 kg/cm² wherein the ethylene is added into the reaction vessel intermittently or continuously in the presence of a catalyst which is prepared by reacting a transition metal compound or a transition metal complex with an organoaluminum compound.

13. A method for producing a branched polyene compound as claimed in claim 12, wherein the conjugated diene compound is represented by the formula (III) wherein $R^1$, $R^2$ and $R^3$ represent hydrogen atoms or alkyl groups of 1–5 carbons; and all of $R^1$, $R^2$ and $R^3$ are not simultaneously hydrogen atoms.

14. A method for producing a branched polyene compound as claimed in claim 12, wherein the conjugated diene compound is represented by the formula (IV)

$$H_2C=CH-\underset{\underset{CH_2}{\|}}{C}-(CH_2)_f-\underset{R^1}{\underset{|}{C}}=\underset{R^2}{\underset{|}{C}}-(CH_2)_n-\underset{R^4}{\underset{|}{C}}=\underset{R^5}{\underset{|}{C}}-R^6 \quad (IV)$$

wherein f is an integer of 1–5; n is an integer of 1–5; $R^1$, $R^2$, $R^4$, $R^5$ and $R^6$ represent hydrogen atoms or alkyl groups of 1–5 carbons; and all of and R are not simultaneously hydrogen atoms.

15. A method for producing a branched polyene compound as claimed in claim 12, wherein the transition metal is selected from the group consisting of iron, cobalt, nickel, rhodium and palladium.

16. A method for producing a branched polyene compound as claimed in claim 12, wherein the transition metal complex is a complex of a transition metal which has 1,2-bis(diphenylphosphino)ethane as ligands, the transition metal being selected from the group consisting of iron, cobalt, nickel, rhodium and palladium.

17. A method for producing a branched polyene compound as claimed in claim 12, wherein the organoaluminum compound is triethylaluminum.

* * * * *